United States Patent [19]

Adachi et al.

[11] Patent Number: 5,183,738
[45] Date of Patent: Feb. 2, 1993

[54] KIT FOR THE DETECTION OF DENATURED LIPOPROTEINS

[75] Inventors: Masakazu Adachi, Takasaki; Toshimitu Saitou, Gunma; Kimiyo Murata, Takasaki; Aki Tamura, Maebashi, all of Japan

[73] Assignee: Japan Immuno Research Laboratories Co., Ltd., Takasaki, Japan

[21] Appl. No.: 413,484

[22] Filed: Sep. 27, 1989

[30] Foreign Application Priority Data

Sep. 29, 1988 [JP] Japan ................... 63-244987

[51] Int. Cl.$^5$ ............... C12Q 1/60; G01N 33/577
[52] U.S. Cl. ..................... 435/7.1; 435/11; 435/962; 436/548; 436/825
[58] Field of Search ........... 436/71, 501, 811, 518, 436/548, 825; 435/7, 91, 803, 7.1, 11, 962; 422/61

[56] References Cited

U.S. PATENT DOCUMENTS

| | | | |
|---|---|---|---|
| 4,211,530 | 7/1980 | Goverde et al. | 422/61 |
| 4,828,986 | 5/1989 | Smith et al. | 435/172.2 |
| 4,966,837 | 10/1990 | Brown et al. | 435/91 |

FOREIGN PATENT DOCUMENTS 0257778 3/1988 European Pat. Off.

OTHER PUBLICATIONS

Chemical Abstracts, vol. 108, No. 13, Mar. 1988 T. Saito et al.
Chemical Abstracts, vol. 107, No. 17, Oct. 1987, S. Ksahara, et al. p. 360.
Chemical Abstracts, vol. 106, No. 26, Jun. 1987, T. Mori et al.

Primary Examiner—Jill A. Johnston
Attorney, Agent, or Firm—Oblon, Spivak, McClelland, Maier & Neustadt

[57] ABSTRACT

A kit and a method for detecting denatured lipoproteins is disclosed. The method comprises: adding to a sample a mixture of (i) an affinity gel with which a monoclonal antibody for apoprotein A-I is coupled and (ii) an affinity gel with which a monoclonal antibody for apoprotein B-100 is coupled; removing apoprotein A-I and apoprotein B-100 in the sample by combining the apoprotein A-I and apoprotein B-100 with the affinity gels; and measuring an amount of lipoproteins in the residue. The kit comprises a mixture of (i) and (ii) as an essential component. The kit and the method is useful for the clinical investigation and diagnosis of abnormal lipid metabolism which can be a cause of heart diseases (e.g. cardiac infarction), diabetes, and various types of atherosclerosis diseases.

7 Claims, 2 Drawing Sheets

KIT FOR THE DETECTION OF DENATURED LIPOPROTEINS

BACKGROUND OF THE INVENTION

1. Field of the Invention

The present invention relates to a kit and a method for detecting denatured lipoproteins, and, more particularly, to a kit and a method for detecting denatured lipoproteins useful for the clinical investigation and diagnosis of abnormal lipid metabolism which can be a cause of heart diseases (e.g. cardiac infarction), diabetes, and various types of atherosclerosis diseases such as cerebrovascular disorders (e.g. cerebral hemorrhage).

2. Description of the Background Art

Abnormal lipid metabolism can be defined as abnormality in either synthesis, secretion, or degradation of lipoproteins. Abnormal lipoprotein metabolism includes congenital abnormality and acquired abnormality.

Abnormal lipid metabolism is considered to be a cause of various diseases such as heart diseases (e.g. cardiac infarction) and various types of atherosclerosis diseases such as cerebrovascular disorders (e.g. cerebral hemorrhage), and to have significant influence on the progress and aftercare of these diseases Detection of abnormal lipid metabolism is thus very important for the clinical investigation and diagnosis of these diseases.

A method most widely accepted for detecting abnormal lipid metabolism is that using the total cholesterol value in blood as a parameter. With this method, the total cholesterol value in blood is measured by a conventional method (e.g, an enzymatic method), and abnormal lipid metabolism is judged to be present if the value falls outside the normal range which was established based on clinical and experiential knowledge In another method used in recent years lipoproteins in blood, i.e., combined lipid-apoproteins, are fractionated by specific gravities, and a cholesterol value for high specific gravity lipoproteins (high density lipoproteins; HDL) is measured. The HDL cholesterol value, or the value obtained by subtracting the HDL cholesterol value from the total cholesterol value (the atherosclerosis index), is used as a parameter for detecting abnormal lipid metabolism.

According to the results of many immunological studies and clinical knowledge accumulated up to the present time, however, these conventional methods of detecting abnormal lipid metabolism do not always exactly reflect the incidence of abnormal lipid metabolism and have only a limited clinical significance. This is because in these methods the total or HDL cholesterol values, which are not necessarily associated with abnormal lipid metabolism, are used. Although the high value of total cholesterol value can be one of the risk factors of ischemic heart diseases [e.g. *Med. Clin. North Am.*, 58, 363-379 (1974)], it does not directly relate to the diseases Occurrence of the diseases in groups with normal lipid metabolism or healthy conditions in groups with highly abnormal lipid metabolism according to these detection methods is not rare. Detection using as a parameter a HDL cholesterol value or using an atherosclerosis index based on the HDL cholesterol value does not always accurately reflect the incidence of disease [*Arterial Scherosis*, 14, (4), 931-936 (1986)].

Many reports have recently surfaced discussing the significance on actual abnormal lipid metabolism of denatured lipoproteins which are produced when lipoproteins such as very low density lipoproteins (VLDL) undergo certain types of actions in vivo [e.g, Hui, D. Y., Innerarity, T. L. and Mahley, R. W., *J. Bio.. Chem.*, 259, 860-869 (1984); Gonen, et al., *Diabetes*, 30, 875 (1981)].

Detection of such denatured lipoproteins can therefore more accurately detect the incidence of abnormal lipid metabolism and is thus considered to be clinically very useful as a diagnostic means for determining diseases involving abnormal lipid metabolism, especially for the early discovery of the diseases and for monitoring the progress or curing effects of the diseases. Details of such denatured lipoproteins are, however, not yet elucidated at the present time and there are no known methods for their detection.

The present inventors have conducted extensive studies in order to develop a method and a kit for accurately detecting abnormal lipid metabolism which can detect various diseases involving abnormal lipid metabolism and can monitor the progress or curing effects of such diseases. As a result, the present inventors found that a portion obtained by excluding lipoproteins constituting apoprotein A-I (Apo A-I-containing lipoprotein) and lipoproteins constituting apoprotein B-100 (Apo B-100-containing lipoprotein) from total plasma lipoproteins corresponded to the above denatured lipoproteins. The inventors further found that the Apo A-I-containing lipoprotein and the Apo B-100-containing lipoprotein could be removed when a blood sample was incubated with affinity gels containing specific antibodies, thus ensuring an accurate and ready measurement or detection of the amount of denatured lipoproteins in the sample. Such a finding has led to the completion of the present invention.

SUMMARY OF THE INVENTION

Accordingly, an object of the present invention is to provide a kit for detecting denatured lipoproteins which comprises as an essential component a mixture of an affinity gel with which a monoclonal antibody for apoprotein A-I is coupled and an affinity gel with which a monoclonal antibody for apoprotein B-100 is coupled.

Another object of the present invention is to provide a method for measuring an amount of denatured lipoproteins which comprises: adding to a sample a mixture of an affinity gel with which a monoclonal antibody for apoprotein A-I is coupled and an affinity gel with which a monoclonal antibody for apoprotein B-100 is coupled; removing apoprotein A-I and apoprotein B-100 in the sample by combining the apoprotein A-I and apoprotein B-100 with the affinity gels; and measuring the amount of lipoproteins in the residue.

Other objects, features and advantages of the invention will hereinafter become more readily apparent from the following description.

DETAILED DESCRIPTION OF THE INVENTION AND PREFERRED EMBODIMENTS

Figure 1:
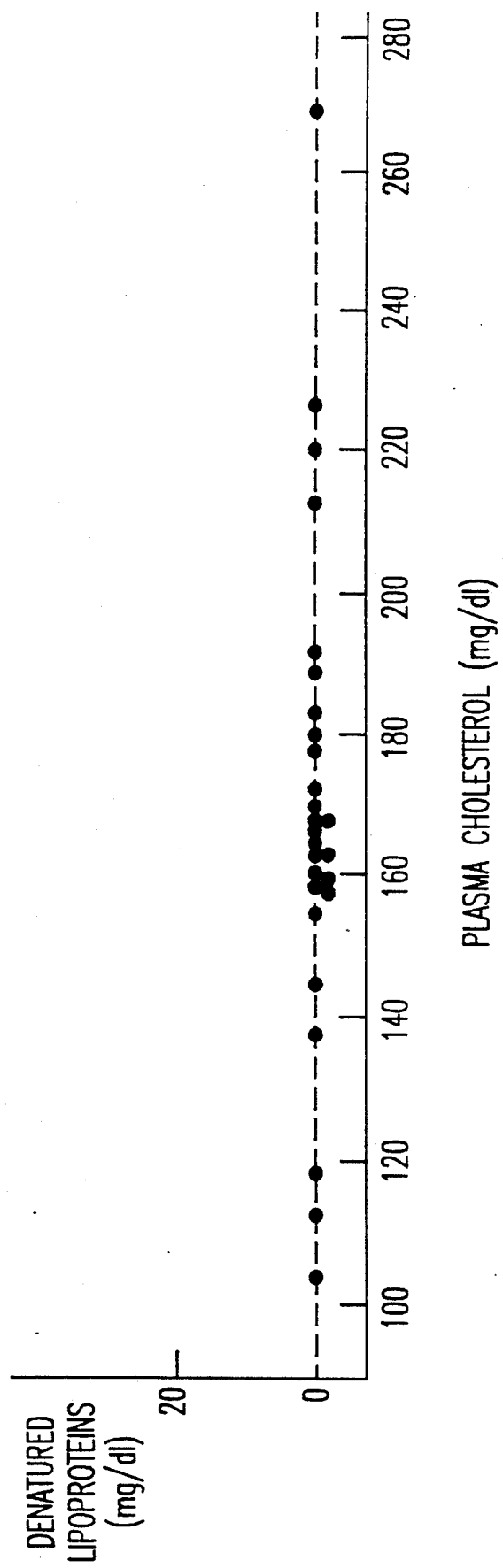
FIG. 1 is a graph showing the correlation between the amounts of denatured lipoproteins measured using the kit of the present invention and the plasma cholesterol values.

The kit of the present invention is designed to measure the amount of denatured lipoproteins, i.e., lipoproteins excluding Apo A-I-containing lipoprotein and Apo B-100-containing lipoprotein, from the total lipoproteins in blood. According to the present invention it is possible to detect abnormal lipid metabolism and to clinically investigate and diagnose various diseases involving abnormal lipid metabolism by using the kit. Since the above denatured lipoproteins are rarely present in blood when lipid metabolism is normal and increase depending on the degree of abnormality of lipid metabolism, their amount in blood accurately reflects any abnormality of the lipid metabolism. Thus, an accurate measurement and detection of abnormal lipid metabolism can be ensured by using the kit of the present invention.

The kit of the present invention as well as the measurement of denatured lipoproteins or the detection of abnormal lipid metabolism by using the kit are described in detail in the following.

A sample used in the detection by using the kit of the present invention is blood. Serum or plasma collected while the subject is under fasting conditions is especially preferable as samples. Samples are prepared for the test according to conventional methods after having been collected from subjects.

Since lipoproteins exist in blood as a combination of a lipid such as a cholesterol, triglyceride, phospholipid, free fatty acid, or the like and an apoprotein, either the total amount of lipids or the total amount of apoprotein can be used for the measurement of the amount of lipoproteins. The cholesterol values for the lipids or for the apoproteins can be determined by an enzymatic method or the like.

A mixture of an affinity gel with which a monoclonal antibody for apoprotein A-I (anti-apoprotein A-I antibody) is coupled and an affinity gel with which a monoclonal antibody for apoprotein B-100 (anti-apoprotein B-100 antibody) is coupled is used as is or packed in a tube which can be shaken or centrifuged. Alternatively, it is desirable to equilibrate the gels in advance with a suitable buffer, for example, with a 0.1M Tris-HCl (pH 7.4)+0.15M NaCl buffer. A conventional preservative such as sodium azide or the like can be added to the buffer.

An affinity gel used in the present invention can be prepared by using a conventional method. Specifically, the anti-apoprotein A-I antibody and the anti-apoprotein B-100 antibody are activated by cyanogen bromide and each is coupled with an affinity gel. The gels are mixed and equilibrated with a suitable buffer solution. Typical examples of antibodies which can be used are anti-humanapo A-I monoclonal antibody and anti-humanapo B-100 monoclonal antibody (both produced by Japan Immunoresearch Lab. Co.). Antibodies are by no means limited to these antibodies in this invention. A typical example of an affinity gel is Sepharose 4B (trade name, product of Pharmacia Co.) activated by cyanogen bromide or the like in advance. A coupling reaction can be carried out according to a method conventionally used for coupling reactions of the above type of gels and proteins, usually at pH range of 8-10 using an antibody in an amount of about 1-10 mg for 1 ml of a gel at room temperature (20-25° C.) within 2 hours.

There are no specific limitations as to the proportion of anti-apoprotein A-I antibody and anti-apoprotein B-100 antibody in the above gel mixture which is the essential component of the kit of this invention. Usually, an equivalent or more, preferably 1-2 times by weight, of anti-apoprotein B-100 antibody is used for anti-apoprotein A-I antibody. It is desirable to adjust the pH value of the gel mixture to about 7-7.5.

If required, a stabilizer such as sucrose, a bovine serum protein, or the like, or a preservative can be added to the kit of the present invention containing the gel mixture as an essential component. A preservative is selected from compounds which will not adversely affect the result obtained by the use of the kit. A typical example is diluted sodium azide. Glycerol or a water-soluble glycerol derivative, alcohol, glycol, glycol ether, or the like can also be added to the kit.

According to a preferred embodiment for detecting denatured lipoproteins by using the kit of the present invention, the affinity gel mixture which is the essential component of the kit is placed in a suitable container or test tube and equilibrated with a suitable buffer. A prescribed amount of serum to be tested is added to the container or the tube and allowed to react at room temperature by being left to stand still. A cholesterol coloring reagent is added to the supernatant. After incubation for a prescribed period of time, an absorbance of the supernatant is measured to determine the amount of lipids or apoproteins contained therein. The amount of denatured lipoproteins in the serum sample is then determined. Usually, about 1/4-1/16 by weight, preferably about 1/8 by weight, of a sample serum is used for the gel mixture of the present invention.

Denatured lipoproteins can be readily measured by the use of the kit of the present invention. The amount of the denatured lipoproteins thus measured can be used as a parameter for detecting abnormal lipid metabolism. Thus, the kit of the present invention provides a ready and effective means for the detection of abnormal lipid metabolism. Since the amount of denatured lipoproteins in blood accurately reflects the abnormality of lipid metabolism and its degree, the kit of the present invention is very useful for the discovery of the above-mentioned diseases and for the monitoring of the progress or curing effects of such diseases. It is especially useful for the accurate and effective detection of heart diseases such as cardiac infarction and various types of obesities which have not previously been detectable by conventional detection methods.

Other features of the invention will become apparent in the course of the following description of the exemplary embodiments which are given for illustration of the invention and are not intended to be limiting thereof.

EXAMPLES

EXAMPLE 1

(1) Blood was collected with the addition of EDTA from a patient while fasting and centrifuged (2,500-3,000 rpm) to obtain plasma. The triglyceride content of the plasma was measured by an enzymatic method using TG-555 (trade name, product of Kyowa Medics Co., Ltd.). The cholesterol content was also determined by an enzymatic method using Mereko Test CHO (trade name, product of Kanto Chemical Co., Ltd.) in a 2 ml/10 µl amount of plasma. The mixture was incubated for 10 minutes at 37° C. The absorbance was measured at 365 nm.

(2) The above plasma (20 μl) was charged into a test tube and to this was added 600 μl of a reaction fluid containing an anti-apo A-I monoclonal antibody and an anti-apo B-100 monoclonal antibody, both coupled with an affinity gel [Sepharose 4B activated by cyanogen bromide; antibodies (as proteins) in 10 mg units were coupled with 1 ml of the gel and each gel was mixed with an equivalent amount of 0.01 M Tris-HCl buffer (pH 7.4)]. The tube was shaken for 30 minutes and then allowed to stand for 15 minutes. 2 ml of Mercko Test CHO color reagent (trade name, product of Kanto Chemical Co., Ltd.) was added to the supernatant and the mixture was incubated for 20 minutes at 37° C. The amount of cholesterol was determined from the absorbance measured at 365 nm.

(3) As a result, triglycerides in plasma were found to have a higher correlation than cholesterols. From this, the possibility was confirmed of detecting denatured lipoproteins reflecting a chylomicron remnant which is an indicator of exogenous abnormal lipid metabolism and abnormal VLDL (β-) which is an indicator of endogenous abnormal lipid metabolism.

(4) The plasma cholesterol values and the denatured lipoprotein values of healthy persons were determined using the same procedures as above. FIG. 1 shows their correlations, in which the amounts of plasma cholesterol (mg/dl) are plotted along the ordinate and the amounts of denatured lipoproteins are plotted along the abscissa (mg/dl).

FIG. 1 demonstrates that in healthy subjects the denatured lipoprotein values are constant having values in the close vicinity of 0 irrespective of the cholesterol values.

(5) For comparison, the denatured lipoprotein values and cholesterol values are determined by the following method without using the above method of the present invention.

In this method, a column packed with an affinity gel coupled with anti-apo A-I monoclonal antibody and a column packed with an affinity gel coupled with anti-apo B-100 monoclonal antibody were used to determine each cholesterol value for apoprotein A-1-containing lipoproteins (absorbed fractions) and apoprotein B-100-containing lipoproteins (absorbed fractions) in plasma. The cholesterol values for denatured lipoproteins were then determined by subtracting the sum of these cholesterol values from the total plasma cholesterol value.

Specifically, each 250 μl of plasma from the same healthy subjects as in (4) above was charged for absorption into the columns packed with an affinity gel coupled with anti-apo A-I monoclonal antibody and an affinity gel coupled with anti-apo B-100 monoclonal antibody. The columns were washed with 20 ml of a 0.1M PBS buffer (pH 7.2) and eluted using 10 ml of a mixed solution of 1M acetic acid and 0.5M NaCl. A ½-fold 3.5M Tris-HCl buffer was added to the eluant. To a 1 ml aliqout of this mixture was added 2 ml of Mereko Test CHO (trade name, product of Kanto Chemical Co., Ltd.). After incubating at 37° C. for 30 minutes, the cholesterol value was measured by absorption at 365 nm.

A parameter (P) was calculated from the cholesterol values measured as above according to the following formula:

$$\text{Parameter (\%)} = 1 - \frac{B + C}{A} \times 100 \quad (I)$$

wherein A is the total plasma cholesterol value (mg/dl), B is the cholesterol value (mg/dl) of apoprotein A-1-containing lipoproteins separated from the plasma, and C is the cholesterol value (mg/dl) of apoprotein B-100-containing lipoproteins separated from the plasma.

The results are shown in the columns designated as "Comparison Measurement" in Table 1, in which the results obtained in (4) above by the use of the kit of the present invention are also presented (in the columns designated as "Invented Measurement").

TABLE 1

| Subject No. | Plasma Cholesterol Value | | Denatured Lipoprotein Value | |
|---|---|---|---|---|
| | Invented Measurement | Comparison Measurement | Invented Measurement | Comparison Measurement (P) |
| 1 | 169 | 159 | 0 | −16 (−10) |
| 2 | 119 | 133 | 0 | 11 (8) |
| 3 | 169 | 188 | 0 | 28 (15) |
| 4 | 166 | 157 | 0 | 13 (8) |
| 5 | 159 | 140 | 0 | 8 (6) |
| 6 | 146 | 219 | 0 | 2 (1) |

The results shown in the above table show that the measurement using the kit of the present invention ensures a more accurate determination of denatured lipoprotein values with smaller fluctuations than the conventional method. The invented method is simple and easy to use and provides excellent results.

EXAMPLE 2

500 mg (2 tablets each containing 250 mg) of Probucol (trade name, produced by Dow Pharmaceutical Co.) was given twice each day in the morning and evening for 98 days to a subject who had a high triglyceride value (TG > 150) and a high total cholesterol value (TC > 250) in the determination in Example 1 (1) and was thus judged to be hyperlipidemic. The triglyceride value and the total plasma cholesterol value as well as the denatured lipoprotein value according to the method of the present invention of the subject were measured in the same manner as in Example 1 before and after the 98-day period.

Figure 2:
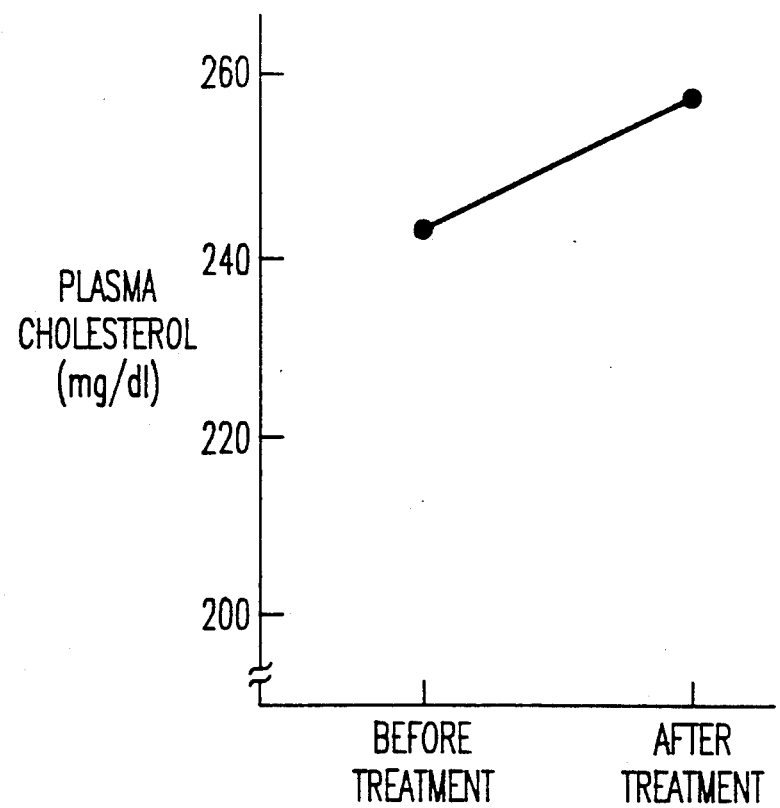
FIG. 2 is a graph showing the plasma cholesterol values of a hyperlipemia patient before and after treatment.
Figure 3:
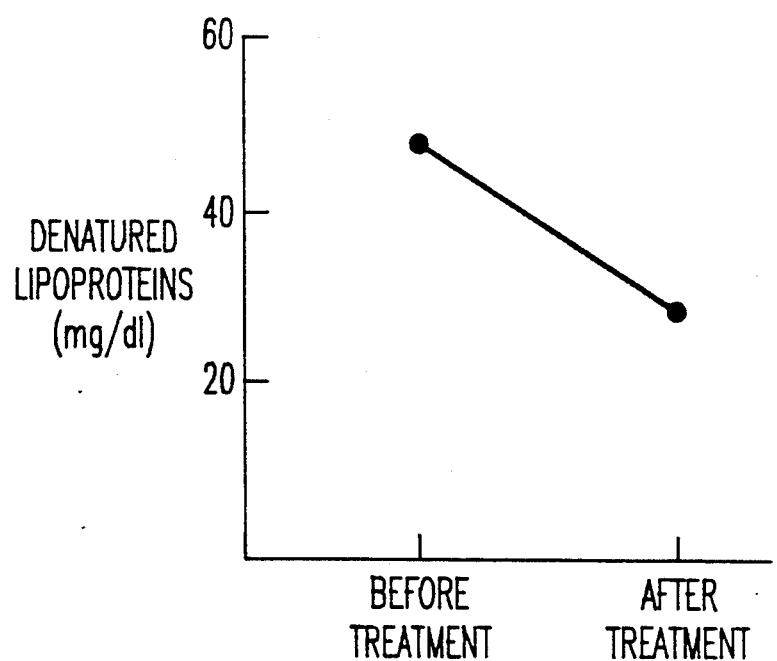
FIG. 3 is a graph showing the amounts of denatured lipoprotein of a hyperlipemia patient before and after treatment.

The triglyceride value changed from 425 (the value before treatment) to 389 (the value after treatment). Changes in the plasma cholesterol value and the denatured lipoprotein value are respectively shown in FIGS. 2 (1) and (2). These data demonstrate that the kit and the method of the present invention ensure accurate determinations of denatured lipoproteins corresponding to symptoms and are useful for the diagnosis of diseases.

EXAMPLE 3

The total cholesterol values (T-CHO), triglyceride values (TG), HDL cholesterol values (HDL-C), and denatured lipoprotein values (DLP-CHO) were measured on each 5-member group suffering from diabetes, ischemic heart disease, and cerebrovascular disorder. T-CHO, TG, and HDL-C were measured by the same methods as described in Example 1. DLP-CHO was measured by the heparin-manganese coupling precipitation method using HDL-cholesterol Wako (trade name, product of Wako Pure Chemical Co., Ltd.). The results are shown in Table 2.

TABLE 2

| Subject No. | T-CHO (mg/dl) | TG (mg/dl) | HDL-C (mg/dl) | DLP-CHO (mg/dl) |
|---|---|---|---|---|
| Diabetes | | | | |
| 1 | 333 | 202 | 45 | 6 |
| 2 | 241 | 202 | 43 | 14 |
| 3 | 167 | 247 | 51 | 5 |
| 4 | 192 | 527 | 40 | 36 |
| 5 | 189 | 179 | 36 | 8 |
| Ischemic heart disease | | | | |
| 1 | 241 | 187 | 47 | 12 |
| 2 | 296 | 812 | 33 | 81 |
| 3 | 198 | 127 | 42 | 8 |
| 4 | 143 | 94 | 59 | 9 |
| 5 | 331 | 190 | 43 | 12 |
| Cerebrovascular disorder | | | | |
| 1 | 198 | 118 | 33 | 10 |
| 2 | 248 | 484 | 37 | 31 |
| 3 | 244 | 138 | 48 | 5 |
| 4 | 178 | 199 | 37 | 6 |
| 5 | 249 | 54 | 40 | 4 |

EXAMPLE 4

Denatured lipoprotein values in the plasma of the hyperlipidemic patients were measured according to the method described in Example 1. The patients were grouped into three types as defined by WHO. The results are shown in Table 3.

TABLE 3

| Types of hyperlipidemic patients | Number of patients | Denatured lipoprotein values* |
|---|---|---|
| IIa | 31 | 2.1 ± 3.9 (mg/dl CHO) |
| IIb | 53 | 20.1 ± 25.0 |
| IV | 16 | 7.7 ± 6.7 |

*Mean value ± S.D.

Obviously, numerous modifications and variations of the present invention are possible in light of the above teachings. It is therefore to be understood that within the scope of the appended claims, the invention may be practiced otherwise than as specifically described herein.

What is claimed is:

1. A method for detecting abnormal lipid metabolism, comprising the steps of:
    contacting a sample containing apoprotein A-I, apoprotein B-100 and denatured lipoproteins with a mixture of a first affinity gel coupled with a monoclonal antibody for said apoprotein A-I and a second affinity gel coupled with a monoclonal antibody for said apoprotein B-100 to remove said apoprotein A-I and said apoprotein B-100 from said sample;
    determining the amount of denatured lipoproteins in said sample; and
    correlating the amount of denatured lipoproteins to abnormal lipid metabolism.

2. The method of claim 1, wherein said determining comprises reacting said sample with an enzyme in a solution after said apoprotein A-I and said apoprotein B-100 are removed, then optically measuring the absorbance of said solution.

3. The method of claim 2, wherein said reacting is conducted in the presence of a cholesterol coloring reagent.

4. The method of claim 1, wherein said sample is blood serum or blood plasma.

5. The method of claim 4, further comprising the step of determining total cholesterol for a portion of said sample prior to said contacting step.

6. The method of claim 1, wherein said first affinity gel and said second affinity gel are activated with cyanogen bromide before being respectively coupled to said monoclonal antibody for said apoprotein A-I and said monoclonal antibody for said apoprotein B-100.

7. The method claim 1, wherein said monoclonal antibody for said apoprotein A-I and said monoclonal antibody for said apoprotein B-100 are activated with cyanogen bromide before being respectively coupled to said first affinity gel and said second affinity gel.

* * * * *